United States Patent
Lant et al.

(10) Patent No.: US 10,287,534 B2
(45) Date of Patent: *May 14, 2019

(54) AUTOMATIC DISHWASHING DETERGENT COMPOSITION

(71) Applicant: The Procter & Gamble Company, Cincinnati, OH (US)

(72) Inventors: Neil Joseph Lant, Newcastle upon Tyne (GB); Philip Frank Souter, Northumberland (GB); David John Tarbit, Newcastle upon Tyne (GB); Torsten Bak Regueira, Vaerlose (DK); Bitten Plesner, Bagsvaerd (DK); Thomas Holberg Blicher, Bagsvaerd (DK); Anne Dorte Houg, Copenhagen S (DK); Sofia Arnehed, Bagsvaerd (DK); Lars Lehmann Hylling Christensen, Bagsvaerd (DK); Carsten Andersen, Bagsvaerd (DK); Euan John Magennis, Tyne and Wear (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,186

(22) Filed: May 3, 2017

(65) Prior Publication Data

US 2017/0321158 A1    Nov. 9, 2017

(30) Foreign Application Priority Data

May 3, 2016   (EP) .................................... 16168201

(51) Int. Cl.

| | | |
|---|---|---|
| C11D 3/386 | (2006.01) | |
| C11D 11/00 | (2006.01) | |
| C11D 3/39 | (2006.01) | |
| C11D 3/37 | (2006.01) | |
| A47L 15/46 | (2006.01) | |
| A47L 15/00 | (2006.01) | |
| A47L 15/44 | (2006.01) | |
| C11D 3/00 | (2006.01) | |
| C11D 3/33 | (2006.01) | |
| C11D 17/04 | (2006.01) | |

(52) U.S. Cl.
CPC .......... *C11D 3/386* (2013.01); *A47L 15/0007* (2013.01); *A47L 15/44* (2013.01); *A47L 15/46* (2013.01); *C11D 3/0073* (2013.01); *C11D 3/33* (2013.01); *C11D 3/378* (2013.01); *C11D 3/38609* (2013.01); *C11D 3/38618* (2013.01); *C11D 3/3905* (2013.01); *C11D 11/0023* (2013.01); *C11D 17/042* (2013.01); *C12Y 302/01001* (2013.01)

(58) Field of Classification Search
None
See application file for complete search history.

(56) References Cited

U.S. PATENT DOCUMENTS

| 5,856,164 A | 1/1999 | Outtrup et al. |
|---|---|---|
| 6,093,562 A | 7/2000 | Bisgard-Frantzen et al. |
| 9,493,730 B2 | 11/2016 | Meek et al. |
| 2006/0199750 A1* | 9/2006 | Berger .................... C11D 1/66 510/220 |
| 2008/0153733 A1* | 6/2008 | Andersen ............... C11D 3/386 510/226 |
| 2011/0195481 A1 | 8/2011 | Svendsen et al. |
| 2014/0045739 A1* | 2/2014 | Baez Chavez ......... C11D 3/386 510/226 |

FOREIGN PATENT DOCUMENTS

| EP | 2100949 | * 4/2015 |
|---|---|---|
| WO | WO 94/22800 | 10/1994 |
| WO | WO 96/23873 | 8/1996 |
| WO | WO 97/41213 | 11/1997 |
| WO | WO 99/23211 | 5/1999 |
| WO | WO 00/37627 | 6/2000 |
| WO | WO 00/60060 | 10/2000 |
| WO | WO 2006/002643 A2 | 1/2006 |
| WO | WO 2015/091959 A2 | 6/2015 |
| WO | WO 2015/189371 A1 | 12/2015 |

OTHER PUBLICATIONS

Chica et al. Curr Opin Biotechnol. Aug. 2005;16(4):378-84.*
Singh et al. Curr Protein Pept Sci. 2017, 18, 1-11.*
Li et al. Biotechnol Bioeng. Jul. 2014;111(7):1273-87. Epub May 6, 2014.*
Accession W4QZ53. Mar. 19, 2014.*
European Search Report for application No. 16168201.8-1358, dated Jul. 28, 2016, 7 pages.
European Search Report for application No. 16168200.0-1358, dated Jul. 14, 2016, 8 pages.

* cited by examiner

*Primary Examiner* — Christian L Fronda

(74) *Attorney, Agent, or Firm* — Andres E. Velarde; Melissa G. Krasovec

(57) ABSTRACT

Bleach-containing automatic dishwashing cleaning composition including a new amylase.

12 Claims, No Drawings

Specification includes a Sequence Listing.

SEQUENCE LISTING

```
<160> NUMBER OF SEQ ID NOS: 1

<210> SEQ ID NO 1
<211> LENGTH: 485
<212> TYPE: PRT
<213> ORGANISM: Bacillus sp. AA560

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300
```

-continued

```
Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
            485
```

US 10,287,534 B2

AUTOMATIC DISHWASHING DETERGENT COMPOSITION

FIELD OF THE INVENTION

The present invention is in the field of detergents. In particular, it relates to an automatic dishwashing detergent composition comprising a new amylase. The composition provides improved stability and improved cleaning versus compositions comprising conventional amylases even at low temperatures and short cycles, making the composition more environmentally friendly than traditional compositions and allowing for a more energy efficient automatic dishwashing processes.

BACKGROUND OF INVENTION

There is a permanent desire to improve the performance of automatic dishwashing compositions, their environmental profile and to reduce the energy required by the automatic dishwashing process. Enzymes are important ingredients in automatic dishwashing compositions. When designing an enzyme for automatic dishwashing several criteria need to be fulfilled. It should be stable in the detergent matrix prior to usage, it should be stable during wash and it should be highly active and fast to act during wash.

The object of the present invention is to provide a more stable automatic dishwashing composition that provide better cleaning and that allows to reduce the temperature and length of automatic dishwashing cycles without impairing on performance

SUMMARY OF THE INVENTION

Position 202 versus amino acid sequence SEQ ID NO:1 has been shown to be important for the stability of amylases in the presence of bleaching agents. Mutations in this position can improve the stability of amylases however the mutations can reduce the activity and kinetic of the amylase. It has been surprisingly found that amylases that do not have mutations on position 202 versus amino acid sequence SEQ ID NO:1 and have mutations in one or more of the following positions versus amino acid sequence SEQ ID NO:1 51, 246 and/or 334, present very good stability, activity and kinetic. Thus, according to the first aspect of the present invention, there is provided an automatic dishwashing cleaning composition comprising an improved amylase. The composition comprises bleach, preferably an inorganic bleach, more preferably percarbonate.

According to the second and third aspects of the invention, there are provided methods of automatic dishwashing, involving short cycles and/or low temperatures allowing for automatic dishwashing processes with improved environmental profiles.

The elements of the composition of the invention described in connection with the first aspect of the invention apply mutatis mutandis to the other aspects of the invention.

DETAILED DESCRIPTION OF THE INVENTION

The present invention encompasses an automatic dishwashing cleaning composition. The composition comprises bleach and an improved amylase and it presents improved stability and delivers improved cleaning versus cleaning compositions comprising conventional amylases. The invention also encompasses methods of automatic dishwashing, involving short cycles and/or low temperatures allowing for automatic dishwashing processes with improved environmental profiles. Amylase performance under short cycles and/or low temperature is more challenging than under conventional long and high temperature cycles.

The amylase of the composition of the invention is herein sometimes referred to as "the amylase of the invention". The amylase having SEQ ID NO:1 is herein sometimes referred to as "the parent amylase".

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

The amylase of the invention, i.e. mutated, amino acids in the amylases of the invention are defined by reference to the amino acid numbering of SEQ ID NO: 1 (which corresponds to AA560 of B. subtilis).

Thus, for purposes of the present invention, the amylase disclosed in SEQ ID NO: 1 is used to determine the corresponding amino acid residue in another amylase. The amino acid sequence of another amylase is aligned with the amylase disclosed in SEQ ID NO: 1, and based on the alignment, the amino acid position number corresponding to any amino acid residue in the amylase disclosed in SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another amylase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAI-FT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), and EMBOSS EMMA employing ClustalW (1.83 or later; Thompson et al., 1994, Nucleic Acids Research 22: 4673-4680), using their respective default parameters.

When the other amylase has diverged from the amylase of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of amylase families (profiles) to search databases. For example, the PSI BLAST program generates profiles through an iterative database search process and is capable of detecting remote homologs (Atschul et al., 1997, Nucleic Acids Res. 25: 3389-3402).

Even greater sensitivity can be achieved if the family or superfamily for the amylase has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the amylase, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567). In describing the amylase variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

The term "mutation", in the context of the amylase of the invention, means that one or more amino acids within the reference amino acid sequence (i.e. SEQ ID NO:1) are altered by substitution with a different amino acid or by deletion. Additionally, the mutation may correspond to an insertion of one or more extra amino acid(s) within the reference amino acid sequence.

The term "variant" means an amylase comprising a mutation, i.e., a substitution, insertion, and/or deletion, at one or more (e.g., several) positions relative to the parent amylase of SEQ ID NO:1. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 90%, preferably at least 95%, more preferably at least 98% of the amylase activity of the amylase of SEQ ID NO: 1.

The term "wild-type" amylase means an amylase expressed by a naturally occurring microorganism, such as a bacterium, yeast, or filamentous fungus found in nature.

The Amylase of the Invention

The amylase of the invention comprises a mutation at one or more (e.g., several) positions within the amino acid sequence of SEQ ID NO: 1. The amylase of the invention exhibits an enhanced wash performance compared to the amylase of SEQ ID NO: 1. The amylase of the invention comprises a mutation in one or more of the following positions: 51, 246 and/or 334 versus SEQ ID NO: 1. Position 202 of SEQ ID NO: 1 remains unchanged. The amylase of the invention has at least 95%, preferably at least 96% and more preferably at least 98% sequence identity to SEQ ID NO: 1.

The amylase of the invention represents variants of the parent alpha amylase of SEQ ID NO: 1, which variants exhibit enhanced wash performance in domestic and/or industrial cleaning processes, such as the laundry cleaning and automatic dishwashing, especially in automatic dishwashing even under stressed conditions such as those found in short cycles and/or low temperatures.

In addition to enhanced wash performance, the amylase of the invention may also exhibit improvements in one or more of the following properties relative to the parent amylase of SEQ ID NO:1:
(i) Substrate specificity;
(ii) Substrate binding;
(iii) Specific activity;
(iv) Thermal stability
(v) pH stability profile;
(vi) Ca2+ dependency;
(vii) Oxidation stability;
(viii) Increased/decreased pI; and/or
(ix) Sensitivity to surfactants.

Assays for determining the above properties of a protein are described in WO 2006/002643, WO 2001/066712 and EP 2 264 460 A.

Preferably the amylase of the invention has mutations versus SEQ ID NO:1 selected from A51T, T246 (I/L/V), S334T and mixtures thereof.

Preferably the amylase comprises one or more, preferably three or more mutations in the following positions versus SEQ ID NO: 1:
9, 149, 182, 186, 257, 295, 299, 323, 339 and 345; and optionally with one or more, preferably all of the mutations in the following positions: 118, 183, 184, 195, 320 and 458, which if present preferably comprise R118K, D183*, G184*, N195F, R320K and/or R458K.

Preferred amylases comprise the following mutations M9L, R118K, G149A, G182T, D183*, G184*, G186A, N195F, T257I, Y295F, N299Y, R320K, M232T, A339S, E345R and R458K.

Preferred amylases comprise mutations versus SEQ ID NO: 1 selected from the group consisting of: A51T, A186D, T246I, S334T, A51T+A186D, A51T+T246I, A51T+S334T, A186D+T246I, A186D+S334T, T246I+S334T, A51T+A186D+T246I, A51T+A186D+S334T, A51T+T246I+S334T, A186D+T246I+S334T, and A51T+A186D+T246I+S334T.

Especially preferred amylase comprises one of the following mutations:
a) T246V;
b) T246I and S334T;
c) T246L and S334T;
d) T246V and S334T; and
e) A51T and T246I and S334T;

Preferred amylases consist of one or more, preferably three or more mutations in the following positions versus SEQ ID NO: 1:
9, 149, 182, 186, 257, 295, 299, 323, 339 and 345; and optionally with one or more, preferably all of the mutations in the following positions: 118, 183, 184, 195, 320 and 458, which if present preferably comprise R118K, D183*, G184*, N195F, R320K and/or R458K in combination with mutations versus SEQ ID NO: 1 selected from the group consisting of: A51T, A186D, T246I, S334T, A51T+A186D, A51T+T246I, A51T+S334T, A186D+T246I, A186D+S334T, T246I+S334T, A51T+A186D+T246I, A51T+ A186D+S334T, A51T+T246I+S334T, A186D+T246I+S334T, and A51T+A186D+T246I+S334T.

Especially preferred amylases amylase comprises the following mutations versus SEQ ID: No 1 M9L, R118K, G149A, G182T, D183*, G184*, G186A, N195F, T257I, Y295F, N299Y, R320K, M232T, A339S, E345R and R458K in combination with one of the following mutations:
a) T246V;
b) T246I and S334T;
c) T246L and S334T;
d) T246V and S334T; and
e) A51T and T246I and S334T;

Preferably, the composition of the invention comprises at least 0.005 mg, preferably from about 0.0025 to about 0.025, more preferably from about 0.05 to about 0.3, especially from about 0.01 to about 0.25 mg of active amylase.

Automatic Dishwashing Cleaning Composition

The automatic dishwashing cleaning composition can be in any physical form. It can be a loose powder, a gel or presented in unit dose form. Preferably it is in unit dose form, unit dose forms include pressed tablets and water-soluble packs. The automatic dishwashing cleaning composition of the invention is preferably presented in unit-dose form and it can be in any physical form including solid, liquid and gel form. The composition of the invention is very well suited to be presented in the form of a multi-compartment pack, more in particular a multi-compartment pack comprising compartments with compositions in different physical forms, for example a compartment comprising a composition in solid form and another compartment comprising a composition in liquid form. The composition is preferably enveloped by a water-soluble film such as polyvinyl alcohol. Especially preferred are compositions in unit dose form wrapped in a polyvinyl alcohol film having a thickness of less than 100 µm. The detergent composition of the invention weighs from about 8 to about 25 grams, preferably from about 10 to about 20 grams. This weight range fits comfortably in a dishwasher dispenser. Even though this range amounts to a low amount of detergent, the detergent has been formulated in a way that provides all the benefits mentioned herein above.

The composition is preferably phosphate free. By "phosphate-free" is herein understood that the composition comprises less than 1%, preferably less than 0.1% by weight of the composition of phosphate.

Preferably, the composition of the invention is phosphate-free and comprises a dispersant polymer and a complexing agent. For the purpose of this invention a "complexing agent" is a compound capable of binding polyvalent ions such as calcium, magnesium, lead, copper, zinc, cadmium, mercury, manganese, iron, aluminium and other cationic polyvalent ions to form a water-soluble complex. The complexing agent has a logarithmic stability constant ([log K]) for Ca2+ of at least 5, preferably at least 6. The stability constant, log K, is measured in a solution of ionic strength of 0.1, at a temperature of 25° C.

Preferably, the composition of the invention comprises an amino-carboxylated complexing agent, preferably selected from the group consisting of methyl-glycine-diacetic acid (MGDA), its salts and derivatives thereof, glutamic-N,N-diacetic acid (GLDA), its salts and derivatives thereof, iminodisuccinic acid (IDS), its salts and derivatives thereof, carboxy methyl inulin, ASDA (L-Aspartic acid N,N-diacetic acid tetrasodium salt), its salts and derivatives thereof its salts and derivatives thereof and mixtures thereof. Especially preferred complexing agent for use herein is selected from the group consisting of MGDA and salts thereof, especially preferred for use herein is the three sodium salt of MGDA. Preferably, the complexing agent is the three sodium salt of MGDA and the dispersant polymer is a sulfonated polymer, more preferably comprising 2-acrylamido-2-methylpropane sulfonic acid monomer.

Dispersant Polymer

A dispersant polymer can be used in any suitable amount from about 0.1 to about 20%, preferably from 0.2 to about 15%, more preferably from 0.3 to % by weight of the composition.

The dispersant polymer is capable to suspend calcium or calcium carbonate in an automatic dishwashing process.

The dispersant polymer has a calcium binding capacity within the range between 30 to 250 mg of Ca/g of dispersant polymer, preferably between 35 to 200 mg of Ca/g of dispersant polymer, more preferably 40 to 150 mg of Ca/g of dispersant polymer at 25° C. In order to determine if a polymer is a dispersant polymer within the meaning of the invention, the following calcium binding-capacity determination is conducted in accordance with the following instructions:

Calcium Binding Capacity Test Method

The calcium binding capacity referred to herein is determined via titration using a pH/ion meter, such as the Meettler Toledo SevenMulti™ bench top meter and a PerfectION™ comb Ca combination electrode. To measure the binding capacity a heating and stirring device suitable for beakers or tergotometer pots is set to 25° C., and the ion electrode with meter are calibrated according to the manufacturer's instructions. The standard concentrations for the electrode calibration should bracket the test concentration and should be measured at 25° C. A stock solution of 1000 mg/g of Ca is prepared by adding 3.67 g of $CaCl_2$-$2H_2O$ into 1 L of deionised water, then dilutions are carried out to prepare three working solutions of 100 mL each, respectively comprising 100 mg/g, 10 mg/g, and 1 mg/g concentrations of Calcium. The 100 mg Ca/g working solution is used as the initial concentration during the titration, which is conducted at 25° C. The ionic strength of each working solution is adjusted by adding 2.5 g/L of NaCl to each. The 100 mL of 100 mg Ca/g working solution is heated and stirred until it reaches 25° C.

The initial reading of Calcium ion concentration is conducted at when the solution reaches 25° C. using the ion electrode. Then the test polymer is added incrementally to the calcium working solution (at 0.01 g/L intervals) and measured after 5 minutes of agitation following each incremental addition. The titration is stopped when the solution reaches 1 mg/g of Calcium. The titration procedure is repeated using the remaining two calcium concentration working solutions.

The binding capacity of the test polymer is calculated as the linear slope of the calcium concentrations measured against the grams/L of test polymer that was added.

The dispersant polymer preferably bears a negative net charge when dissolved in an aqueous solution with a pH greater than 6.

The dispersant polymer can bear also sulfonated carboxylic esters or amides, in order to increase the negative charge at lower pH and improve their dispersing properties in hard water. The preferred dispersant polymers are sulfonated/carboxylated polymers, i.e., polymer comprising both sulfonated and carboxylated monomers.

Preferably, the dispersant polymers are sulfonated derivatives of polycarboxylic acids and may comprise two, three, four or more different monomer units. The preferred copolymers contain:

At least one structural unit derived from a carboxylic acid monomer having the general formula (III):

wherein $R_1$ to $R_3$ are independently selected from hydrogen, methyl, linear or branched saturated alkyl groups having from 2 to 12 carbon atoms, linear or branched mono or polyunsaturated alkenyl groups having from 2 to 12 carbon atoms, alkyl or alkenyl groups as aforementioned substituted with —NH2 or —OH, or —COOH, or $COOR_4$, where $R_4$ is selected from hydrogen, alkali metal, or a linear or branched, saturated or unsaturated alkyl or alkenyl group with 2 to 12 carbons;

Preferred carboxylic acid monomers include one or more of the following: acrylic acid, maleic acid, maleic anhydride, itaconic acid, citraconic acid, 2-phenylacrylic acid, cinnamic acid, crotonic acid, fumaric acid, methacrylic acid, 2-ethylacrylic acid, methylenemalonic acid, or sorbic acid. Acrylic and methacrylic acids being more preferred.

Optionally, one or more structural units derived from at least one nonionic monomer having the general formula (IV):

Wherein $R_5$ to $R_7$ are independently selected from hydrogen, methyl, phenyl or hydroxyalkyl groups containing 1 to 6 carbon atoms, and can be part of a cyclic structure, X is an optionally present spacer group which is selected from —$CH_2$—, —COO—, —CONH— or —$CONR_8$—, and $R_8$ is selected from linear or branched, saturated alkyl radicals having 1 to 22 carbon atoms or unsaturated, preferably aromatic, radicals having from 6 to 22 carbon atoms.

Preferred non-ionic monomers include one or more of the following: butene, isobutene, pentene, 2-methylpent-1-ene, 3-methylpent-1-ene, 2,4,4-trimethylpent-1-ene, 2,4,4-trimethylpent-2-ene, cyclopentene, methylcyclopentene, 2-methyl-3-methyl-cyclopentene, hexene, 2,3-dimethylhex-1-ene, 2,4-dimethylhex-1-ene, 2,5-dimethylhex-1-ene, 3,5-dimethylhex-1-ene, 4,4-dimethylhex-1-ene, cyclohexene, methylcyclohexene, cycloheptene, alpha olefins having 10 or more carbon atoms such as, dec-1-ene, dodec-1-ene, hexadec-1-ene, octadec-1-ene and docos-1-ene, preferred aromatic monomers are styrene, alpha methylstyrene, 3-methylstyrene, 4-dodecylstyrene, 2-ethyl-4-bezylstyrene, 4-cyclohexylstyrene, 4-propylstyrol, 1-vinylnaphtalene, 2-vinylnaphtalene; preferred carboxylic ester monomers are methyl (meth)acrylate, ethyl (meth)acrylate, propyl (meth)acrylate, t-butyl (meth)acrylate, pentyl (meth)acrylate, hexyl (meth)acrylate, 2-ethylhexyl (meth)acrylate, octyl (meth)acrylate, lauryl (meth)acrylate, stearyl (meth)acrylate and behenyl (meth)acrylate; preferred amides are N-methyl acrylamide, N-ethyl acrylamide, N-t-butyl acrylamide, N-2-ethylhexyl acrylamide, N-octyl acrylamide, N-lauryl acrylamide, N-stearyl acrylamide, N-behenyl acrylamide.

and at least one structural unit derived from at least one sulfonic acid monomer having the general formula (V) and (VI):

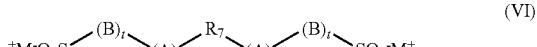

wherein $R_7$ is a group comprising at least one sp2 bond, A is O, N, P, S, an amido or ester linkage, B is a mono- or polycyclic aromatic group or an aliphatic group, each t is independently 0 or 1, and M+ is a cation. In one aspect, $R_7$ is a C2 to C6 alkene. In another aspect, R7 is ethene, butene or propene.

Preferred sulfonated monomers include one or more of the following: 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propen-1-sulfonic acid, styrenesulfonic acid, vinylsulfonic acid, 3-sulfopropyl, 3-sulfo-propylmethacrylate, sulfomethacrylamide, sulfomethylmethacrylamide and mixtures of said acids or their water-soluble salts.

Preferably, the polymer comprises the following levels of monomers: from about 40 to about 90%, preferably from about 60 to about 90% by weight of the polymer of one or more carboxylic acid monomer; from about 5 to about 50%, preferably from about 10 to about 40% by weight of the polymer of one or more sulfonic acid monomer; and optionally from about 1% to about 30%, preferably from about 2 to about 20% by weight of the polymer of one or more non-ionic monomer. An especially preferred polymer comprises about 70% to about 80% by weight of the polymer of at least one carboxylic acid monomer and from about 20% to about 30% by weight of the polymer of at least one sulfonic acid monomer.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

The carboxylic acid is preferably (meth)acrylic acid. The sulfonic acid monomer is preferably 2-acrylamido-2-propanesulfonic acid (AMPS).

Preferred commercial available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas.

Suitable dispersant polymers include anionic carboxylic polymer of low molecular weight. They can be homopolymers or copolymers with a weight average molecular weight of less than or equal to about 200,000 g/mol, or less than or equal to about 75,000 g/mol, or less than or equal to about 50,000 g/mol, or from about 3,000 to about 50,000 g/mol, preferably from about 5,000 to about 45,000 g/mol. The dispersant polymer may be a low molecular weight homopolymer of polyacrylate, with an average molecular weight of from 1,000 to 20,000, particularly from 2,000 to 10,000, and particularly preferably from 3,000 to 5,000.

The dispersant polymer may be a copolymer of acrylic with methacrylic acid, acrylic and/or methacrylic with maleic acid, and acrylic and/or methacrylic with fumaric acid, with a molecular weight of less than 70,000. Their molecular weight ranges from 2,000 to 80,000 and more preferably from 20,000 to 50,000 and in particular 30,000 to 40,000 g/mol. and a ratio of (meth)acrylate to maleate or fumarate segments of from 30:1 to 1:2.

The dispersant polymer may be a copolymer of acrylamide and acrylate having a molecular weight of from 3,000 to 100,000, alternatively from 4,000 to 20,000, and an acrylamide content of less than 50%, alternatively less than 20%, by weight of the dispersant polymer can also be used. Alternatively, such dispersant polymer may have a molecular weight of from 4,000 to 20,000 and an acrylamide content of from 0% to 15%, by weight of the polymer.

Dispersant polymers suitable herein also include itaconic acid homopolymers and copolymers. Alternatively, the dispersant polymer can be selected from the group consisting of alkoxylated polyalkyleneimines, alkoxylated polycarboxylates, polyethylene glycols, styrene co-polymers, cellulose sulfate esters, carboxylated polysaccharides, amphiphilic graft copolymers and mixtures thereof.

Bleach

The composition of the invention preferably comprises from about 1 to about 20%, more preferably from about 5 to about 18%, even more preferably from about 8 to about 15% of bleach by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein.

Typical organic bleaches are organic peroxyacids, especially dodecanediperoxoic acid, tetradecanediperoxoic acid, and hexadecanediperoxoic acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 12 carbon atoms, in particular from 2 to 10 carbon atoms, and/or optionally substituted perbenzoic acid. Suitable substances bear O-acyl and/or N-acyl groups of the number of carbon atoms specified and/or optionally substituted benzoyl groups.

Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), decanoyloxybenzoic acid (DOBA), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). If present the composition of the invention comprises from 0.01 to 5, preferably from 0.2 to 2% by weight of the composition of bleach activator, preferably TAED.

Bleach Catalyst

The composition herein preferably contains a bleach catalyst, preferably a metal containing bleach catalyst. More preferably the metal containing bleach catalyst is a transition metal containing bleach catalyst, especially a manganese or cobalt-containing bleach catalyst.

Bleach catalysts preferred for use herein include manganese triazacyclononane and related complexes; Co, Cu, Mn and Fe bispyridylamine and related complexes; and pentamine acetate cobalt(III) and related complexes.

Preferably the composition of the invention comprises from 0.001 to 0.5, more preferably from 0.002 to 0.05% of bleach catalyst by weight of the composition. Preferably the bleach catalyst is a manganese bleach catalyst.

Inorganic Builder

The composition of the invention preferably comprises an inorganic builder. Suitable inorganic builders are selected from the group consisting of carbonate, silicate and mixtures thereof. Especially preferred for use herein is sodium carbonate. Preferably the composition of the invention comprises from 5 to 50%, more preferably from 10 to 40% and especially from 15 to 30% of sodium carbonate by weight of the composition.

Surfactant

Surfactants suitable for use herein include non-ionic surfactants, preferably the compositions are free of any other surfactants. Traditionally, non-ionic surfactants have been used in automatic dishwashing for surface modification purposes in particular for sheeting to avoid filming and spotting and to improve shine. It has been found that non-ionic surfactants can also contribute to prevent redeposition of soils.

Preferably the composition of the invention comprises a non-ionic surfactant or a non-ionic surfactant system, more preferably the non-ionic surfactant or a non-ionic surfactant system has a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated nonionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

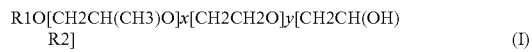

$$R1O[CH2CH(CH3)O]_x[CH2CH2O]_y[CH2CH(OH)R2] \quad (I)$$

wherein R1 is a linear or branched, aliphatic hydrocarbon radical having from 4 to 18 carbon atoms; R2 is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH2CH(OH)R2]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

Enzymes

In describing enzyme variants herein, the following nomenclature is used for ease of reference: Original amino acid(s):position(s):substituted amino acid(s). Standard enzyme IUPAC 1-letter codes for amino acids are used.

Proteases

Suitable proteases include metalloproteases and serine proteases, including neutral or alkaline microbial serine proteases, such as subtilisins (EC 3.4.21.62) as well as chemically or genetically modified mutants thereof. Suitable proteases include subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii*.

Especially preferred proteases for the detergent of the invention are polypeptides demonstrating at least 90%, preferably at least 95%, more preferably at least 98%, even more preferably at least 99% and especially 100% identity with the wild-type enzyme from *Bacillus lentus*, comprising mutations in one or more, preferably two or more and more preferably three or more of the following positions, using the BPN' numbering system and amino acid abbreviations as illustrated in WO00/37627, which is incorporated herein by reference: V68A, N87S, S99D, S99SD, S99A, S101G, S101M, S103A, V104N/I, G118V, G118R, S128L, P129Q, S130A, Y167A, R170S, A194P, V205I and/or M222S.

Most preferably the protease is selected from the group comprising the below mutations (BPN' numbering system) versus either the PB92 wild-type (SEQ ID NO:2 in WO 08/010925) or the subtilisin 309 wild-type (sequence as per PB92 backbone, except comprising a natural variation of N87S).

(i) G118V+S128L+P129Q+S130A
(ii) S101M+G118V+S128L+P129Q+S130A
(iii) N76D+N87R+G118R+S128L+P129Q+S130A+S188D+N248R
(iv) N76D+N87R+G118R+S128L+P129Q+S130A+S188D+V244R
(v) N76D+N87R+G118R+S128L+P129Q+S130A
(vi) V68A+N87S+S101G+V104N Suitable commercially available protease enzymes include those sold under the trade names Savinase®, Polarzyme®, Kannase®, Ovozyme®, Everlase® and Esperase® by Novozymes A/S (Denmark), those sold under the tradename Properase®, Purafect®, Purafect Prime®, Purafect Ox®, FN3®, FN4®, Excellase®, Ultimase® and Purafect OXP® by Genencor International, those sold under the tradename Opticlean® and Optimase® by Solvay Enzymes, those available from Henkel/ Kemira, namely BLAP.

Preferred levels of protease in the composition of the invention include from about 0.2 to about 2 mg of active protease per grams of the composition.

Other Amylases

In addition to the amylase of the invention the composition of the invention can comprise other amylases. A preferred alkaline amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in U.S. Pat. No. 5,856,164 and WO99/23211, WO 96/23873, WO00/60060 and WO 06/002643, especially the variants with one or more substitutions in the following positions versus the AA560 SEQ ID No. 1:
9, 26, 30, 33, 82, 37, 106, 118, 128, 133, 149, 150, 160, 178, 182, 186, 193, 195, 202, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, preferably that also contain the deletions of D183* and G184*.
(b) variants exhibiting at least 95% identity with the wild-type enzyme from *Bacillus* sp. 707 (SEQ ID NO:7 in U.S. Pat. No. 6,093,562), especially those comprising one or more of the following mutations M202, M208, S255, R172, and/or M261. Preferably said amylase comprises one of M202L or M202T mutations.

Suitable commercially available alpha-amylases include DURAMYL®, LIQUEZYME®, TERMAMYL®, TERMAMYL ULTRA®, NATALASE®, EVEREST®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, EXCELLENZ™ S series, including EXCELLENZ™ S 1000 and EXCELLENZ™ S 2000 and PURASTAR OXAM® (DuPont Industrial Biosciences., Palo Alto, Calif.) and KAM® (Kao, 14-10 Nihonbashi Kayabacho, 1-chome, Chuo-ku Tokyo 103-8210, Japan). Amylases especially preferred for use herein include NATALASE®, STAINZYME®, STAINZYME PLUS®, EXCELLENZ™ S 1000, EXCELLENZ™ S2000 and mixtures thereof.

Preferably, the composition of the invention comprises at least 0.005 mg, preferably from about 0.0025 to about 0.025, more preferably from about 0.05 to about 0.3, especially from about 0.01 to about 0.25 mg of active amylase.

Preferably, the protease and/or amylase of the composition of the invention are in the form of granulates, the granulates comprise more than 29% of sodium sulfate by weight of the granulate and/or the sodium sulfate and the active enzyme (protease and/or amylase) are in a weight ratio of between 3:1 and 100:1 or preferably between 4:1 and 30:1 or more preferably between 5:1 and 20:1.

Crystal Growth Inhibitor

Crystal growth inhibitors are materials that can bind to calcium carbonate crystals and prevent further growth of species such as aragonite and calcite.

Especially preferred crystal growth inhibitor for use herein is HEDP (1-hydroxyethylidene 1,1-diphosphonic acid). Preferably, the composition of the invention comprises from 0.01 to 5%, more preferably from 0.05 to 3% and especially from 0.5 to 2% of a crystal growth inhibitor by weight of the product, preferably HEDP.

Metal Care Agents

Metal care agents may prevent or reduce the tarnishing, corrosion or oxidation of metals, including aluminium, stainless steel and non-ferrous metals, such as silver and copper.

Preferably the composition of the invention comprises from 0.1 to 5%, more preferably from 0.2 to 4% and especially from 0.3 to 3% by weight of the product of a metal care agent, preferably the metal care agent is benzo triazole (BTA).

Glass Care Agents

Glass care agents protect the appearance of glass items during the dishwashing process. Preferably the composition of the invention comprises from 0.1 to 5%, more preferably from 0.2 to 4% and specially from 0.3 to 3% by weight of the composition of a metal care agent, preferably the glass care agent is a zinc containing material, specially hydrozincite.

The automatic dishwashing composition of the invention preferably has a pH as measured in 1% weight/volume aqueous solution in distilled water at 20° C. of from about 9 to about 12, more preferably from about 10 to less than about 11.5 and especially from about 10.5 to about 11.5.

The automatic dishwashing composition of the invention preferably has a reserve alkalinity of from about 10 to about 20, more preferably from about 12 to about 18 at a pH of 9.5 as measured in NaOH with 100 grams of product at 20° C.

A preferred automatic dishwashing composition of the invention include:
i) from 2 to 20% by weight of the composition of bleach, preferably sodium percarbonate;
ii) preferably a bleach activator, more preferably TAED;
iii) enzymes, preferably amylases and proteases;
iv) optionally but preferably from 5 to 30% by weight of the composition of an inorganic builder, preferably sodium carbonate;
v) optionally but preferably from 2 to 10% by weight of the composition of a non-ionic surfactant;
vi) optionally but preferably a bleach catalyst, more preferably a manganese bleach catalyst;
vii) other optional ingredients include: a crystal growth inhibitor, preferably HEDP, and glass care agents.

EXAMPLES

Two automatic dishwashing detergent compositions were made comprising the ingredients detailed herein below, Composition 1 comprising an amylase according to the invention and composition 2 comprising a commercially available amylase outside of the scope of the invention as a comparative reference. The solid and liquid ingredients were added at the beginning of the wash.

| Ingredients (grams of active material) | Composition 1 According to the invention | Composition 2 Comparative reference |
|---|---|---|
| Solid ingredients | | |
| Sodium carbonate | 4.00 | 4.00 |
| MGDA | 6.00 | 6.00 |
| Sodium percarbonate | 2.00 | 2.00 |
| Sulfonated polymer | 1.2 | 1.2 |
| Protease | 0.034 | 0.034 |
| Amylase 2 | | 0.087 |
| Amylase 1 | 0.087 | |
| Bleach catalyst | 0.009 | 0.009 |
| Miscellaneous | balance to 15.53 | balance to 15.53 |
| Liquid ingredients | | |
| Lutensol ® TO7 | 1.165 | 1.165 |
| Plurafac ® LF224 | 0.5826 | 0.5826 |
| Miscellaneous | balance to 1.8 | balance to 1.8 |

MGDA Tri-sodium methyl glycine diacetate supplied by BASF
Amylase 2 Stainzyme® Plus supplied by Novozymes
Amylase 1 Amylase according to the invention comprising mutation T246V
Protease Protease supplied by DuPont
Bleach catalyst Pentaamineacetatocobalt (III) nitrate
Plurafac® LF224 Nonionic surfactant supplied by BASF
Sulfonated polymer Acusol® 588 supplied by Dow Chemical
Lutensol® TO7 Nonionic surfactant supplied by BASF
Cleaning Test in a Short Cycle Compositions 1 and 2 were compared for their cleaning performance using mixed starch (DM77) CFT tiles (Center For Testmaterials BV, Stoomloggerweg 11, 3133 KT Vlaardingen, the Netherlands), which are stained melamine dishwasher monitors that discriminate the performance of the product to remove enzyme sensitive stains.

Two tiles per wash of mixed starch were placed on the top rack of the dishwasher (Miele 1022 dishwashing machine) at the beginning of the wash at the same time as the dishwashing detergent compositions. The inlet water was artificially softened water (through an ion exchange column) with a total level of 10 $CaCO_3$ ppm. The dishwashers were set into a 40° C. short cycle with a total duration of 35 minutes, including rinses and drying stages. The test was repeated three more times using new tiles each time. At the end the eight tiles were evaluated using a computer aided image analysis, which measured the L-a-b values of the stain before and after the wash, this data was used to assign a stain removal index, having a continuous scale from 0 to a 100, where 0% is unwashed and 100% is a complete removal of the stain.

| | Composition 1 | Composition 2 |
|---|---|---|
| DM77 Mixed starch, coloured | 70.5 | 58.7 |

The data shows that the dishwashing detergent composition 1, according to the invention, has an improved starch removal performance vs. the comparative composition in a short cycle.

Cleaning Test in a Normal Cycle.

Compositions 1 and 2 were compared for their cleaning performance using double mixed starch, coloured (DM277) CFT tiles (Center For Testmaterials BV, Stoomloggerweg 11, 3133 KT Vlaardingen, the Netherlands), which are stained melamine dishwasher monitors that discriminate the performance of the product to remove enzyme sensitive stains.

Two tiles per wash of double mixed starch were placed on the top rack of the dishwasher (Miele 1022 dishwashing machine) at the beginning of the wash at the same time as the dishwashing detergent compositions. The inlet water was artificially softened water (through an ion exchange column) with a total level of 10 $CaCO_3$ ppm. The dishwashers were set into a 50° C. normal cycle with a total duration of 81 minutes, including rinses and drying stages. The test was repeated three more times using new tiles each time. At the end the eight tiles were evaluated using a computer aided image analysis, which measured the L-a-b values of the stain before and after the wash, this data was used to assign a stain removal index, having a continuous scale from 0 to a 100, where 0% is unwashed and 100% is a complete removal of the stain.

| | Composition 1 | Composition 2 |
|---|---|---|
| DM277 Double Mixed starch, coloured | 70.0 | 42.3 |

The data shows that the dishwashing detergent composition 1, according to the invention, has an improved starch removal performance vs. the comparative composition in a normal cycle.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bleach-containing automatic dishwashing cleaning composition comprising an amylase wherein the amylase is a variant of a parent amylase having the amino acid sequence of SEQ ID NO:1 and the amylase has at least 90% identity with the amino acid sequence of SEQ ID NO:1 wherein the amylase comprises the mutation T246V and the position 202 comprises a methionine.

2. A composition according to claim 1 wherein the amylase comprises one of the following additional mutations:
   a) T246I and S334T;
   b) T246L and S334T;
   c) 246V and S334T; and
   d) A51T and T246I and S334T.

3. A composition according to claim 1 wherein the amylase further comprises the following mutations M9L, R118K, G149A, G182T, D183*, G184*, G186A, N195F, T257I, Y295F, N299Y, R320K, M232T, A339S, E345R and R458K.

4. A composition according to claim 1 wherein the composition is phosphate free.

5. A composition according to claim 1 wherein the composition comprises a dispersant polymer.

6. A composition according to claim 1 wherein the composition comprises a carboxylated/sulfonated polymer.

7. A composition according to claim 1 comprising a complexing agent selected from the group consisting of methyl glycine diacetic acid, its salts and derivatives thereof, glutamic-N,N-diacetic acid, its salts and derivatives thereof, iminodisuccinic acid, its salts and derivatives thereof, carboxy methyl inulin, its salts and derivatives thereof, and mixtures thereof.

8. A composition according to claim 1 wherein the composition comprises a manganese bleach catalyst.

9. A composition according to claim 1 wherein the composition comprises a crystal growth inhibitor.

10. A composition according to claim 1 comprising a protease.

11. A composition according to claim 1 comprising:
   a) from about 0.025 to about 0.3 mg of amylase per gram of the composition;
   b) from about 0.2 to about 2 mg of protease per gram of the composition;
   c) from about 5 to about 20% by weight of the composition of bleach;
   d) from about 1 to about 40% by weight of the composition of a complexing agent;
   e) from about 1 to about 10% by weight of the composition of a dispersant polymer; and
   wherein the composition is phosphate free.

12. A composition according to claim 1 wherein the composition is in unit dose form.

* * * * *